(12) United States Patent
Umeda

(10) Patent No.: US 7,318,337 B2
(45) Date of Patent: Jan. 15, 2008

(54) METHOD AND APPARATUS FOR MEASURING FREQUENCY CHARACTERISTICS OF ACCELERATION SENSOR

(75) Inventor: Akira Umeda, Suginami-ku (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 11/491,277

(22) Filed: Jul. 24, 2006

(65) Prior Publication Data

US 2006/0260398 A1    Nov. 23, 2006

Related U.S. Application Data

(62) Division of application No. 10/509,630, filed as application No. PCT/JP03/04132 on Mar. 31, 2003, now Pat. No. 7,165,440.

(30) Foreign Application Priority Data

Mar. 29, 2002    (JP)    ............................. 2002-097191

(51) Int. Cl.
*G01P 21/00*    (2006.01)
(52) U.S. Cl. ....................................... 73/1.38
(58) Field of Classification Search .................. 73/1.38
See application file for complete search history.

(56) References Cited

U.S. PATENT DOCUMENTS 3,830,091 A    8/1974    Sinsky
5,000,030 A    3/1991    Umeda et al.
5,042,302 A    8/1991    Soelkner
5,952,554 A    9/1999    Umeda
6,286,359 B1    9/2001    Umeda
7,076,991 B2    7/2006    Umeda

FOREIGN PATENT DOCUMENTS

| JP | 3-109165 | 11/1991 |
|---|---|---|
| JP | 04-093653 | 3/1992 |
| JP | 5-273232 | 10/1993 |

(Continued)

OTHER PUBLICATIONS

U.S. Appl. No. 10/509,628, filed Apr. 6, 2005, Umeda.

(Continued)

*Primary Examiner*—Robert Raevis
(74) *Attorney, Agent, or Firm*—Oblon, Spivak, McClelland, Maier & Neustadt, P.C.

(57) ABSTRACT

A metal rod guide (30) supports a metal rod (1) that can be inclined at an arbitrary angle, the support is instantaneously released to produce a free fall state, and during the release period, a first end surface (2) of the metal rod is impacted by a projectile (3) at the same angle as the metal rod, generating an elastic wave pulse in the metal rod. A direct current acceleration sensor (23) detects an acceleration arising when the elastic wave pulse reflects at the other end surface (22) of the metal rod. A strain gauge (25) provided on a side surface of the metal rod and/or a laser interferometer (24) measure strain and end surface motion and the measured values are processed to obtain a frequency response of the direct current acceleration sensor and measure frequency characteristics of the direct current acceleration sensor.

15 Claims, 1 Drawing Sheet

FOREIGN PATENT DOCUMENTS

| | | |
|---|---|---|
| JP | 09-053912 | 2/1997 |
| JP | 09-222484 | 8/1997 |
| JP | 09-2511031 | 9/1997 |

OTHER PUBLICATIONS

U.S. Appl. No. 10/554,620, filed Oct. 27, 2005, Umeda.
U.S. Appl. No. 11/491,277, filed Jul. 24, 2006, Umeda.
Endevco Model 2271A/AM20 Piezoelectric Accelerometer, Product Brochure, May 13, 2003, 2 pages.
Hidetaka Imai, Umeda Akira, Investigation about a highly precise acceleration speed instrumentation system (from 1994 to 1996), ministry of International Trade and Industry Agency of Industrial Science of Technology, a collection of special memoirs, 1997. 113-117 pages.
Ueda Kazunaga, Umeda Akira, Investigation about Patent evaluation method of an acceleration meter with Davis stick (the first report, frequency characteristics valuation law of an accelertion meter with a strain gauge), Japan Society of Mechanical Engineers Collected papers C, 57 533, 143-147 pages.
PTO 06-349 English language translation of Umeda, Japanese Kokai Patent Application No. Hei 1[1992]-93653.
PTO 06-3084 English language translation of Umeda et al., "Frequency Characteristics of Accelerometers Measured by Impact in Low Frequencies".
Umeda Akira, Ueda Kazunaga, About frequency characteristics evaluation method by bombardment of an acceleration speed sensor in a low acceleration domain, Japan Society of Mechanical Engineers, No. 4 design engineering/a system category lecture, Lecture collected papers, 477-482 pages.

METHOD AND APPARATUS FOR MEASURING FREQUENCY CHARACTERISTICS OF ACCELERATION SENSOR

CROSS-REFERENCE TO RELATED APPLICATIONS

The present application is a divisional of U.S. application Ser. No. 10/509,630 filed on Mar. 29, 2005 now U.S. Pat. No. 7,165,440, and in turn claims priority to JP2002-097191 filed on Mar. 29, 2002, the entire contents of each of which are hereby incorporated herein by reference.

TECHNICAL FIELD

The present invention relates to an acceleration sensor used in fields in which it is essential to measure the acceleration, such as of car crash safety testing, robots, transportation equipment, equipment relating to nuclear power generation, ships and space and aeronautical equipment and the like. It particularly relates to a method and apparatus for measuring the frequency characteristics of direct type acceleration sensors where it is particularly important to evaluate the frequency characteristics and the effect of gravity, such as acceleration sensors used in seismographs, car suspensions, measurement of aseismatic characteristics of building structures and inertial navigation systems.

BACKGROUND ART

Acceleration sensors are used in a wide range of fields, including, for example, car crash safety testing, robots, transportation equipment, equipment relating to nuclear power generation, and space and aeronautical equipment and the like. In particular, unlike the alternating current type that only detects the amount of change in acceleration, acceleration sensors used in seismographs, car suspensions, measurement of aseismatic characteristics of building structures and inertial navigation systems and the like are of the so-called direct current type that detects the acceleration of a set value (hereafter called "direct current acceleration sensor").

In such direct current acceleration sensors, conventionally the acceleration sensor that is the standard measurement object is a piezoelectric type acceleration sensor. However, piezoelectric type acceleration sensors are acceleration sensors (hereafter called "alternating current acceleration sensors") that can only detect alternating current acceleration; as yet, no calibration apparatus has been developed that calibrates using shock acceleration an acceleration sensor, as used in a seismograph or the like, that detects acceleration from direct current acceleration.

Conventionally, a technique of installing an acceleration sensor on a single axis vibration table and using a laser interferometer to measure the motion of the vibration table has been regarded as having the highest reliability and has been used as the primary standard. As a technique for generating shock acceleration, there has been proposed a technique in which a metal projectile is launched from a simple tube to impact the end of a rod, generating an elastic wave pulse in the rod, and an acceleration sensor attached to the other end surface of the rod is used to evaluate the frequency characteristics using the shock acceleration generated when the pulse reflects at the other end surface of the rod.

The above technique of impacting a projectile against the end of a rod has a drawback in that, since the duration time of the elastic wave generated in the rod cannot be controlled, the duration time of the generated shock acceleration is too short and there is too much spread in the frequency band.

Also, because a direct current acceleration sensor is subject to the effect of gravity, it has been impossible to clarify the effect that the acceleration applied as a direct current component has on the frequency characteristics. That is, although it is necessary to examine the effect that installation location and ground slope have on the characteristics of a direct current acceleration sensor on which gravity acceleration is applied as the direct current component, such as that used in a seismograph, there has been no technology that satisfies that necessity.

Moreover, when calibrating a direct current accelerometer, the direct current accelerometer can be attached to a vibration table and low shock acceleration generated by the vibration table, but even if low shock acceleration is generated in a vertical direction, it is very difficult to suppress acceleration generated in a horizontal direction.

Also, the above technique of impacting a projectile against a metal rod merely generates an elastic wave pulse in the metal rod, so it has not been possible to control the frequency band of the generated shock acceleration.

In view of the above, an object of the present invention is to provide a method of measuring the frequency characteristics of a direct current acceleration sensor that enables the shock acceleration waveform and frequency band to be freely controlled and readily enables accurate measurement and evaluation including evaluation of the effect that gravity acceleration has on the frequency characteristics of a direct current acceleration sensor that detects direct current acceleration, and an apparatus that implements the method.

Another object of the present invention is to provide a method of calibrating an acceleration sensor by generating shock acceleration in which the duration time, peak value, waveform, waveform spectrum and the like of the acceleration waveform applied to the acceleration sensor that is to be calibrated are readily controlled, and a calibration apparatus.

The present invention is intended to resolve the above problems in accordance with the basic concept described below. That is, the center axis of a metal rod that propagates an elastic wave pulse is disposed in the direction of gravity acceleration. Acceleration is generated in the process of the reflection of the elastic wave pulse that propagates in the metal rod at the end surface.

In order to prevent the distortion of the elastic wave pulse, the metal rod holding function is disabled for the very short time (10 ms or below) that is called the pulse reflection time. Even if the holding is disabled for a short time, owing to the inertia of the rod, the distance it falls can be almost ignored.

A data acquisition method and signal processing is used to deal with dynamic characteristics (gain characteristics, phase characteristics) of the direct current acceleration sensor at a specific frequency.

The effect that differences in the direction of gravity acceleration have on the frequency characteristics of the direct current acceleration sensor can be found by inclining a metal rod that propagates the elastic wave pulse and a projectile launch tube disposed along the same axis.

The effect that an inclination of the table to which the direct current acceleration sensor is attached has on the frequency characteristics of the direct current acceleration sensor can be found by comparing the frequency characteristics when the metal rod is inclined with the frequency characteristics when it is not inclined.

Furthermore, multiple projectile launch tubes are used to control the frequency band of the elastic wave produced in the metal rod. As it is an elastic wave so the principle of superposition applies, it is possible to control the frequency band of the generated acceleration by controlling the projectile launch timing and by controlling the elastic wave pulse duration time.

The above-described basic concept can be implemented by employing the specific method and apparatus of the present invention described below.

The present invention provides a method for measuring frequency characteristics of a direct current acceleration sensor comprising supporting a metal rod with a center axis thereof aligned with a direction of gravity acceleration, impacting one of end surfaces of the metal rod with a projectile to generate and propagate an elastic wave pulse in the metal rod, using a direct current acceleration sensor provided on the other of the end surfaces of the metal rod to detect an acceleration arising when the elastic wave pulse reflects at the other end surface of the metal rod, using a strain gauge provided on a side surface of the metal rod to measure metal rod strain caused by the impact of the projectile against the other end surface of the metal rod, and obtaining a frequency response of the direct current acceleration sensor from a signal from the direct current acceleration sensor and a signal from the strain gauge.

The present invention also provides a method for measuring frequency characteristics of a direct current acceleration sensor comprising supporting a metal rod with a center axis thereof aligned with a direction of gravity acceleration, impacting one of end surfaces of the metal rod with a projectile to generate and propagate an elastic wave pulse in the metal rod, using a direct current acceleration sensor provided on the other of the end surfaces of the metal rod to detect an acceleration arising when the elastic wave pulse reflects at the other end surface of the metal rod, using an optical measuring instrument to measure a velocity of motion of the other end surface of the metal rod arising when the elastic wave pulse reflects at the other end surface of the metal rod, and obtaining a frequency response of the direct current acceleration sensor from a signal from the direct current acceleration sensor and a signal from the optical measuring instrument.

The present invention also provides a method for measuring frequency characteristics of a direct current acceleration sensor comprising supporting a metal rod with a center axis thereof inclined at a prescribed angle to a direction of gravity acceleration, impacting one of end surfaces of the metal rod with a projectile to generate and propagate an elastic wave pulse in the metal rod, using a direct current acceleration sensor provided on the other of the end surfaces of the metal rod to detect an acceleration arising when the elastic wave pulse reflects at the other end surface of the metal rod, using a strain gauge provided on a side surface of the metal rod to measure metal rod strain caused by the impact of the projectile against the other end surface of the metal rod, and obtaining from a signal from the direct current acceleration sensor and a signal from the strain gauge a frequency response of the direct current acceleration sensor, with the direct current acceleration sensor affected by the gravity acceleration, and comparing data of the frequency response with data of the frequency response of the direct current acceleration sensor obtained by the first mentioned method, thereby obtaining characteristics with respect to the gravity acceleration in the frequency response of the direct current acceleration sensor.

The present invention also provides a method for measuring frequency characteristics of a direct current acceleration sensor comprising supporting a metal rod with a center axis thereof inclined at a prescribed angle to a direction of gravity acceleration, impacting one of end surfaces of the metal rod with a projectile to generate and propagate an elastic wave pulse in the metal rod, using a direct current acceleration sensor provided on the other of the end surfaces of the metal rod to detect an acceleration arising when the elastic wave pulse reflects at the other end surface of the metal rod, using an optical measuring instrument to measure a velocity of motion of the other end surface of the metal rod arising when the elastic wave pulse reflects at the other end surface of the metal rod, and obtaining from a signal from the direct current acceleration sensor and a signal from the optical measuring instrument a frequency response of the direct current acceleration sensor in a state in which the gravity acceleration affects the direct current acceleration sensor and comparing data of the frequency response with data of the frequency response of the direct current acceleration sensor obtained by the second mentioned method, thereby obtaining characteristics with respect to gravity acceleration in the frequency response of the direct current acceleration sensor.

The present invention also provides a method for measuring frequency characteristics of a direct current acceleration sensor comprising supporting a metal rod with a center axis thereof aligned with a direction of gravity acceleration, releasing support of the metal rod to produce a free fall state, during a period of releasing the support of the metal rod, impacting one of end surfaces of the metal rod with a projectile to generate and propagate an elastic wave pulse in the metal rod, using a direct current acceleration sensor provided on the other of the end surfaces of the metal rod to detect an acceleration arising when the elastic wave pulse reflects at the other end surface of the metal rod, using a strain gauge provided on a side surface of the metal rod to measure metal rod strain caused by the impact of the projectile against one of the end surfaces of the metal rod, supporting the metal rod immediately after measuring the strain, and obtaining a frequency response of the direct current acceleration sensor from a signal from the direct current acceleration sensor and a signal from the strain gauge.

The present invention also provides a method for measuring frequency characteristics of a direct current acceleration sensor comprising supporting a metal rod with a center axis thereof aligned with a direction of gravity acceleration, releasing support of the metal rod to produce a free fall state, during a period of releasing the support of the metal rod, impacting one of end surfaces of the metal rod with a projectile to generate and propagate an elastic wave pulse in the metal rod, using a direct current acceleration sensor is provided on the other of the end surfaces of the metal rod to detect an acceleration arising when the elastic wave pulse reflects at the other end surface of the metal rod, using an optical measuring instrument to measure a velocity of motion of the other end surface of the metal rod arising when the elastic wave pulse reflects at the other end surface of the metal rod, supporting the metal rod immediately after measuring the velocity of motion, and obtaining a frequency response of the direct current acceleration sensor from a signal from the direct current acceleration sensor and a signal from the optical measuring instrument.

Any one of the first, third and fifth mentioned methods for measuring the frequency characteristics of the direct current acceleration sensor, in which the one end surface of the metal rod is impacted with the projectile to generate the elastic wave pulse in the metal rod, further comprises taking as an input signal to the direct current acceleration sensor provided on the other end surface of the metal rod dynamic displacement, velocity or acceleration in a direction normal to the other end surface produced when the elastic wave pulse generated by the impact of the projectile reflects at the other end surface, using the direct current acceleration sensor to detect, and the strain gauge provided on the side surface of the metal rod to measure, the input signal as a function of time, carrying out signal processing with respect to an output signal from the direct current acceleration sensor and an output signal from the strain gauge, and using data that has been signal processed as a basis for measuring gain-frequency characteristics, phase-frequency characteristics and peak sensitivity of the direct current acceleration sensor in respect of each of dynamic displacement detection function, velocity detection function and acceleration detection function of the direct current acceleration sensor.

Any of the first, third and fifth mentioned methods for measuring the frequency characteristics of the direct current acceleration sensor, in which the one end surface of the metal rod is impacted with the projectile to generate the elastic wave pulse in the metal rod, further comprises taking as an input signal to the direct current acceleration sensor provided on the other end surface of the metal rod dynamic displacement, velocity or acceleration in a direction normal to the other end surface produced when the elastic wave pulse generated by the impact of the projectile reflects at the other end surface, using the direct current acceleration sensor to detect, and the strain gauge provided on the side surface of the metal rod to measure, the input signal as a function of time, carrying out signal processing of an output signal from the direct current acceleration sensor and an output signal from the strain gauge, carrying out error correction of the output signal from the strain gauge based on elastic wave theory, and using data that has been signal processed and error corrected as a basis for measuring gain-frequency characteristics, phase-frequency characteristics and peak sensitivity of the direct current acceleration sensor in respect of each of dynamic displacement detection function, velocity detection function and acceleration detection function of the direct current acceleration sensor.

Any one of the second, fourth and sixth mentioned methods for measuring the frequency characteristics of the direct current acceleration sensor, in which the one end surface of the metal rod is impacted with the projectile to generate the elastic wave pulse in the metal rod, further comprises taking as an input signal to the direct current acceleration sensor provided on the other end surface of the metal rod dynamic displacement, velocity or acceleration in a direction normal to the other end surface produced when the elastic wave pulse generated by the impact of the projectile reflects at the other end surface, using the direct current acceleration sensor to detect, and the optical measuring instrument to directly measure, the input signal as a function of time, carrying out signal processing with respect to an output signal from the direct current acceleration sensor and the output signal from the optical measuring instrument, and using data that has been signal processed as a basis for measuring gain-frequency characteristics, phase-frequency characteristics and peak sensitivity of the direct current acceleration sensor in respect of each of dynamic displacement detection function, velocity detection function and acceleration detection function of the direct current acceleration sensor.

Any one of the first, third and fifth mentioned methods for measuring the frequency characteristics of the direct current acceleration sensor, in which the one end surface of the metal rod is impacted with the projectile to generate the elastic wave pulse in the metal rod, further comprises taking as an input signal to the direct current acceleration sensor provided on the other end surface of the metal rod dynamic displacement, velocity or acceleration in a direction normal to the other end surface produced when the elastic wave pulse generated by the impact of the projectile reflects at the other end surface, using the direct current acceleration sensor to detect, and the strain gauge provided on the side surface of the metal rod to measure, the input signal as a function of time, carrying out signal processing of an output signal from the direct current acceleration sensor and an output signal from the strain gauge, carrying out error correction of the output signal from the strain gauge based on elastic wave theory, using a correction function relating to dynamic characteristics of the strain gauge to correct results of measurements by the gauge, and using data that has been signal processed, error corrected and measurement-result-corrected as a basis for measuring gain-frequency characteristics, phase-frequency characteristics and peak sensitivity of the direct current acceleration sensor in respect of each of dynamic displacement detection function, velocity detection function and acceleration detection function of the direct current acceleration sensor.

In any one of the seventh, eighth and tenth mentioned methods for measuring the frequency characteristics of the direct current acceleration sensor, the strain gauge provided on the side surface of the metal rod is composed of a plurality of strain gauges provided at different distances from the one end surface of the metal rod, or a plurality of strain gauges provided on a circumference of the metal rod at equal distances from the one end surface of the metal rod in any one of seventh, eighth, tenth and eleventh mentioned method.

In any one of the seventh to eleventh mentioned methods for measuring the frequency characteristics of the direct current acceleration sensor, the projectile that impacts the one end surface of the metal rod is composed of a plurality of round, concentric projectiles launched from a launch apparatus that includes multiple round, concentric launch tubes, in which the launch apparatus can precisely and independently control launch timing of each projectile launched.

The present invention further provides an apparatus for measuring frequency characteristics of a direct current acceleration sensor comprising a metal rod support apparatus that supports a metal rod with a center axis thereof aligned with a direction of gravity acceleration, a launch apparatus for impacting one of end surfaces of a metal rod with a projectile to propagate an elastic wave pulse in the metal rod, a direct current acceleration sensor provided on the other of the end surfaces of the metal rod to detect an acceleration arising when the elastic wave pulse reflects at the other end surface of the metal rod, a strain gauge provided on a side surface of the metal rod to measure metal rod strain caused by the impact of the projectile against the other end surface of the metal rod, and a processor for calculating a frequency response of the direct current acceleration sensor from a signal from the direct current acceleration sensor and a signal from the strain gauge.

The present invention also provides an apparatus for measuring frequency characteristics of a direct current acceleration sensor comprising a metal rod support apparatus that supports a metal rod with a center axis thereof aligned with a direction of gravity acceleration, a launch apparatus for impacting one of end surfaces of a metal rod with a projectile to propagate an elastic wave pulse in the metal rod, a direct current acceleration sensor provided on the other of the end surfaces of the metal rod to detect an acceleration arising when the elastic wave pulse reflects at the other end surface of the metal rod, an optical measuring instrument for measuring a velocity of motion of the other end surface of the metal rod arising when the elastic wave pulse reflects at the other end surface of the metal rod, and a processor for calculating a frequency response of the direct current acceleration sensor from a signal from the direct current acceleration sensor and a signal from the optical measuring instrument.

The present invention also provides an apparatus for measuring frequency characteristics of a direct current acceleration sensor comprising a metal rod support apparatus that supports a metal rod with a center axis thereof inclined at a prescribed angle to a direction of gravity acceleration, a launch apparatus for impacting one of end surfaces of the metal rod with a projectile to propagate an elastic wave pulse in the metal rod, a direct current acceleration sensor provided on the other of the end surfaces of the metal rod to detect an acceleration arising when the elastic wave pulse reflects at the other end surface of the metal rod, a strain gauge provided on a side surface of the metal rod to measure metal rod strain caused by the impact of the projectile against the other end surface of the metal rod, and a processor that obtains a frequency response of the direct current acceleration sensor, with the direct current acceleration sensor affected by the gravity acceleration, from a signal from the direct current acceleration sensor and a signal from the strain gauge and compares data of the frequency response of the direct current acceleration sensor with data of the frequency response calculated by the processor in the first mentioned apparatus to calculate characteristics with respect to the gravity acceleration in the frequency response of the direct current acceleration sensor.

The present invention also provides an apparatus for measuring frequency characteristics of a direct current acceleration sensor comprising a metal rod support apparatus that supports a metal rod with a center axis thereof inclined at a prescribed angle to a direction of gravity acceleration, a launch apparatus for impacting one of end surfaces of the metal rod with a projectile to generate and propagate an elastic wave pulse in the metal rod, a direct current acceleration sensor provided on the other of the end surfaces of the metal rod to detect an acceleration arising when the elastic wave pulse reflects at the other end surface of the metal rod, an optical measuring instrument for measuring a velocity of motion of the other end surface of the metal rod arising when the elastic wave pulse reflects at the other end surface of the metal rod, and a processor that obtains a frequency response of the direct current acceleration sensor, with the direct current acceleration sensor affected by the gravity acceleration, from a signal from the direct current acceleration sensor and a signal from the optical measuring instrument and compares data of the frequency response of the direct current acceleration sensor with data of the frequency response calculated by the processor in the second mentioned apparatus to calculate characteristics with respect to the gravity acceleration in the frequency response of the direct current acceleration sensor.

The present invention also provides an apparatus for measuring frequency characteristics of a direct current acceleration sensor comprising a metal rod support apparatus that supports a metal rod with a center axis thereof aligned with a direction of gravity acceleration, releases support of the metal rod to produce a free fall state and re-supports it after a prescribed time, a launch apparatus that during a period of releasing the support of the metal rod impacts one of end surfaces of the metal rod with a projectile to generate an elastic wave pulse in the metal rod, a direct current acceleration sensor provided on the other of the end surfaces of the metal rod to detect an acceleration arising when the elastic wave pulse reflects at the other end surface of the metal rod, a strain gauge provided on a side surface of the metal rod to measure metal rod strain caused by the impact of the projectile against the other end surface of the metal rod, and a processor for calculating a frequency response of the direct current acceleration sensor from a signal from the direct current acceleration sensor and a signal from the strain gauge.

The present invention also provides an apparatus for measuring frequency characteristics of a direct current acceleration sensor comprising a metal rod support apparatus that supports a metal rod with a center axis thereof aligned with a direction of gravity acceleration, releases support of the metal rod to produce a free fall state and re-supports it after a prescribed time, a launch apparatus that during a period of releasing the support of the metal rod impacts one of end surfaces of the metal rod with a projectile to generate an elastic wave pulse in the metal rod, a direct current acceleration sensor provided on the other of the end surfaces of the metal rod to detect an acceleration arising when the elastic wave pulse reflects at the other end surface of the metal rod during the period of releasing the support of the metal rod, an optical measuring instrument for measuring a velocity of motion of the other end surface of the metal rod arising when the elastic wave pulse reflects at the other end surface of the metal rod, and a processor for calculating a frequency response of the direct current acceleration sensor from a signal from the direct current acceleration sensor and a signal from the optical measuring instrument.

In any one of the first, third and fifth mentioned apparatus for measuring frequency characteristics of a direct current acceleration sensor including the launch apparatus for impacting the one end surface of the metal rod with the projectile to generate the elastic wave pulse in the metal rod, the direct current acceleration sensor detects an input signal as a function of time standing for dynamic displacement, velocity or acceleration in a direction normal to the other end surface produced when the elastic wave pulse generated by the impact of the projectile reflects at the other end surface of the metal rod, which input signal constitutes an input signal to the direct current acceleration sensor provided on the other end surface, the strain gauge provided on the side surface of the metal rod measures metal rod strain caused by the impact of the projectile against the other end surface of the metal rod, and the processor carries out signal processing with respect to an output signal from the direct current acceleration sensor and an output signal from the strain gauge and uses data that has been signal processed as a basis for measuring gain-frequency characteristics, phase-frequency characteristics and peak sensitivity of the direct current acceleration sensor in respect of each of dynamic displacement detection function, velocity detection function and acceleration detection function of the direct current acceleration sensor.

In any one of the first, third and fifth mentioned apparatus for measuring frequency characteristics of a direct current acceleration sensor including the launch apparatus for impacting the one end surface of the metal rod with the projectile to generate the elastic wave pulse in the metal rod, the direct current acceleration sensor detects an input signal as a function of time standing for dynamic displacement, velocity or acceleration in a direction normal to the other end surface produced when the elastic wave pulse generated by the impact of the projectile reflects at the other end surface of the metal rod, which input signal constitutes an input signal to the direct current acceleration sensor provided on the other end surface of the metal rod, the strain gauge provided on the side surface of the metal rod measures metal rod strain caused by the impact of the projectile against the other end surface of the metal rod, and the processor carries out signal processing with respect to an output signal from the direct current acceleration sensor and an output signal from the strain gauge, carries out error correction of the output signal from the strain gauge based on elastic wave theory, and uses data that has been signal processed and error corrected as a basis for measuring gain-frequency characteristics, phase-frequency characteristics and peak sensitivity of the direct current acceleration sensor in respect of each of dynamic displacement detection function, velocity detection function and acceleration detection function of the direct current acceleration sensor.

In any one of the second, fourth and sixth mentioned apparatus for measuring frequency characteristics of a direct current acceleration sensor including the launch apparatus for impacting the one end surface of the metal rod with the projectile to generate the elastic wave pulse in the metal rod, the direct current acceleration sensor detects an input signal as a function of time standing for dynamic displacement, velocity or acceleration in a direction normal to the other end surface produced when the elastic wave pulse generated by the impact of the projectile reflects at the other end surface of the metal rod, which input signal constitutes an input signal to the direct current acceleration sensor provided on the other end surface, the optical measuring instrument directly detects the input signal, and the processor carries out signal processing with respect to an output signal from the direct current acceleration sensor and an output signal from the optical measuring instrument and uses data that has been signal processed as a basis for measuring gain-frequency characteristics, phase-frequency characteristics and peak sensitivity of the direct current acceleration sensor in respect of each of dynamic displacement detection function, velocity detection function and acceleration detection function of the direct current acceleration sensor.

In any one of the first, third and fifth mentioned apparatus for measuring frequency characteristics of a direct current acceleration sensor including the launch apparatus for impacting the one end surface of the metal rod with the projectile to generate the elastic wave pulse in the metal rod, the direct current acceleration sensor detects an input signal as a function of time standing for dynamic displacement, velocity or acceleration in a direction normal to the other end surface produced when the elastic wave pulse generated by the impact of the projectile reflects at the other end surface of the metal rod, which input signal constitutes an input signal to the direct current acceleration sensor provided on the other end surface, the strain gauge provided on the side surface of the metal rod measures metal rod strain caused by the impact of the projectile against the other end surface of the metal rod, and the processor carries out signal processing with respect to an output signal from the direct current acceleration sensor and an output signal from the strain gauge, carries out error correction of the output signal from the strain gauge based on elastic wave theory, and uses data that has been signal processed and error corrected as a basis for measuring gain-frequency characteristics, phase-frequency characteristics and peak sensitivity of the direct current acceleration sensor in respect of each of dynamic displacement detection function, velocity detection function and acceleration detection function of the direct current acceleration sensor.

In any one of the seventh, eighth and tenth mentioned apparatus for measuring frequency characteristics of a direct current acceleration sensor, the strain gauge provided on the side surface of the metal rod is composed of a plurality of strain gauges provided at different distances from the one end surface of the metal rod, or a plurality of strain gauges provided at equal distances from the one end surface of the metal rod in any one of the seventh, eighth, tenth and eleventh mentioned apparatus.

In any one of the apparatus for measuring frequency characteristics of a direct current acceleration sensor, the projectile that impacts the one end surface of the metal rod is composed of a plurality of round, concentric projectiles launched from the launch apparatus that includes multiple round, concentric launch tubes, and the launch apparatus can precisely and independently control launch timing of each projectile launched.

In any one of the apparatus for measuring frequency characteristics of a direct current acceleration sensor, the launch tube in the launch apparatus that launches the projectile has a surface treated to reduce friction with the projectile.

In any one of the apparatus for measuring frequency characteristics of a direct current acceleration sensor, the apparatus for measuring the frequency characteristics of the direct current acceleration sensor measures frequency characteristics from shock acceleration in a low peak, narrow frequency band region of the direct current acceleration sensor.

In any one of the second, fourth, sixth, ninth and fourteenth mentioned apparatus for measuring frequency characteristics of a direct current acceleration sensor, the optical measuring instrument comprises a laser interferometer.

In the twelfth mentioned apparatus for measuring frequency characteristics of an acceleration sensor, the one end surface of the metal rod contacts a metal ball and the launch apparatus that launches a plurality of projectiles in a concentric circle from the multiple launch tubes precisely controls launch timing with respect to the metal ball, to generate an elastic wave pulse in the metal rod.

In any one of the first to fifteenth mentioned apparatus for measuring frequency characteristics of an acceleration sensor, the projectile has a structure that is a lamination of different materials to control a frequency band of the elastic wave pulse generated in the metal rod by the impact of the projectile.

In any one of the first to fifteenth mentioned apparatus for measuring frequency characteristics of an acceleration sensor, in accordance with a theoretical propagation of the elastic wave in the metal rod, when obtaining transient signal distortion of an elastic wave pulse from the strain gauge output signal incident on the one end surface, at least a primary term or up to a high-order term of a series-expanded Skalak's analytic solution is used.

In any one of the apparatus for measuring frequency characteristics of an acceleration sensor, the direct current acceleration sensor has a peak sensitivity determined in accordance with an input acceleration waveform and frequency band produced by a plurality of projectiles launched from the launch apparatus with precisely controlled launch timing.

As described above, in accordance with the present invention, an elastic wave pulse is generated in a metal rod supported in alignment with a direction of gravity acceleration or at a prescribed angle thereto by impacting a projectile against one end surface of the metal rod, an acceleration sensor is used to measure the acceleration of the motion of the other end surface of the metal rod, a laser interferometer or strain gauge is used to measure the motion of the other end surface, the measurement signal is processed and corrected, and the processed result and the measured values obtained by the acceleration sensor are used to obtain the frequency response of the acceleration sensor. Therefore, the shock acceleration waveform and the frequency band can be freely controlled and the frequency characteristics of the direct current acceleration sensor that detects the direct current acceleration can be accurately and easily measured and evaluated, including evaluation of the effect of the gravity acceleration. Also, the duration time, peak value, waveform spectra and the like of the acceleration waveform imparted with respect to the direct current acceleration sensor to be calibrated can be readily controlled, enabling shock acceleration to be generated and the direct current acceleration sensor to be calibrated.

BEST MODE FOR CARRYING OUT THE INVENTION

Figure 1:
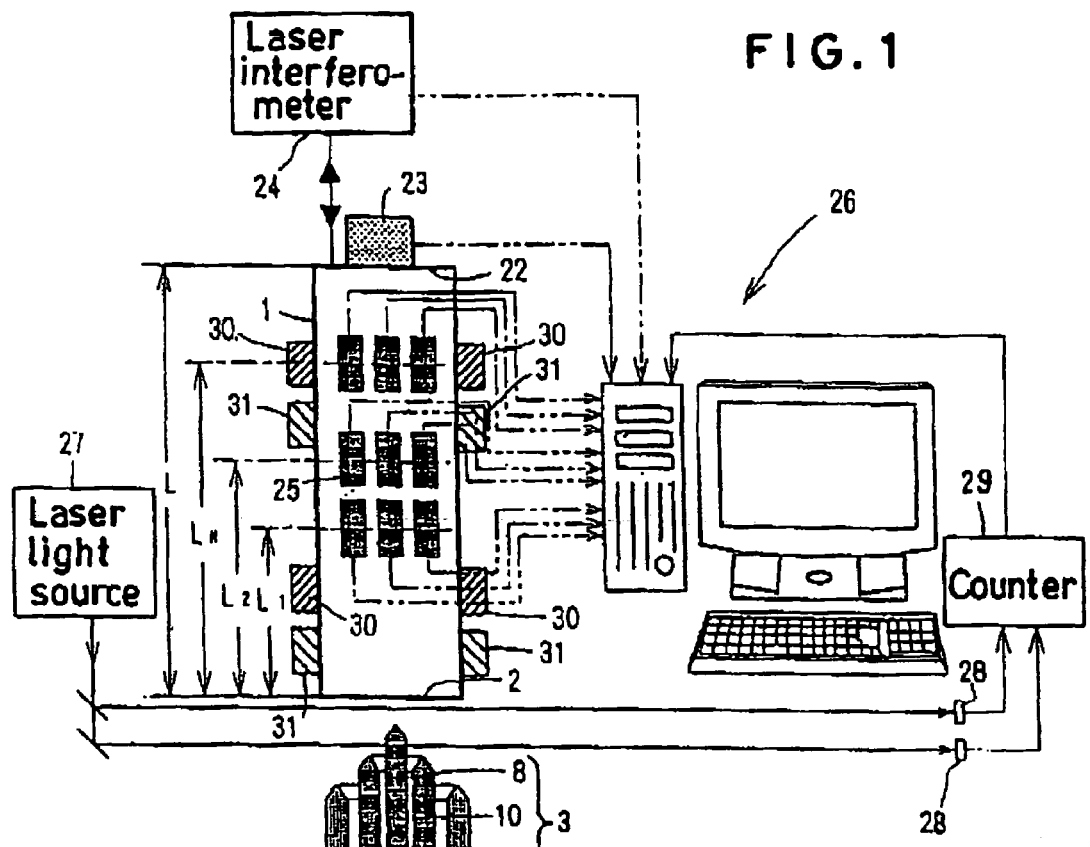
FIG. 1 is a schematic view of an apparatus for implementing the method for measuring the frequency characteristics of a direct current acceleration sensor according to the present invention.

FIG. 1 illustrates an embodiment of an apparatus for implementing the method for measuring the frequency characteristics of a direct current acceleration sensor of this invention. A metal rod 1 is set at a prescribed inclined angle by a non-contact type metal rod guide 30. In the illustrated embodiment, the metal rod 1 is set to be vertical. In this state, the metal rod 1 is fixedly held by a metal rod support apparatus 31 so that the vertical position may be kept; it can be released from this holding state for a very short time, and then immediately held again. A projectile 3, described later, is used to impact a first end surface 2 of the metal rod 1 to apply a shock, generating an elastic wave pulse therein. In doing this, a multiple launch tube 7 having n (n=1 . . . N, innermost being 1, outermost being N) tubes is used. In the illustrated embodiment, the multiple launch tube 7 has three launch tubes: a center launch tube 4, a middle launch tube 5 and an outer launch tube 6. A multiplicity of n (n=1 . . . N, innermost being 1, outermost being N) projectiles 3 are launched from this multiple launch tube 7.

In the illustrated embodiment, a cylindrical first projectile 8 can be independently launched from the interior of the center launch tube 4 by a first launch apparatus 9, an annular second projectile 10 can be independently launched from the annular space between the center launch tube 4 and the middle launch tube 5 by a second launch apparatus 11, and an annular third projectile 12 can be independently launched from the annular space between the middle launch tube 5 and the outer launch tube 6 by a third launch apparatus 13. The launch status can be detected by projecting in front of the metal rod 1 a pair of separated laser beams from a laser light source 27, using light receiving elements 28, 28 to detect an interruption of these laser beams, using a counter 29 to measure the time difference thereof, and inputting the data to a personal computer 26. By means of a launch tube inclined support apparatus 32, a launch apparatus 14 is inclined at the same angle as the angle of inclination at which a non-contact type metal rod guide 30 is set.

In the launch of each of the above projectiles from the launch apparatus 14, a valve controller 15 opens a first valve 16, supplying high-pressure air from a first high-pressure air source 17 to the first launch apparatus 9 to thereby launch the first projectile 8 in the center launch tube 4 toward the first end surface 2 of the metal rod 1. When the first projectile 8 collides against the first end surface 2 of the metal rod 1, an elastic pulse waveform is produced within the metal rod 1 that propagates in the metal rod 1.

The valve controller 15 also opens a second valve 18 a prescribed time $\alpha 1$ after opening the first valve 16, supplying high-pressure air from a second high-pressure air source 19 to the second launch apparatus 11, whereby the annular second projectile 10 located between the center launch tube 4 and the middle launch tube 5 is launched toward the first end surface 2 of the metal rod 1. When the second projectile 10 collides against the first end surface 2 of the metal rod 1, inside the metal rod 1, an elastic pulse waveform is generated and propagates in the metal rod 1 with a time-lag of $\alpha 1$ relative to the waveform generated by the collision of the first projectile 8.

Similarly, the valve controller 15 also opens a third valve 20 a prescribed time $\alpha 2$ after opening the first valve 16, supplying high-pressure air from a third high-pressure air source 21 to the third launch apparatus 13, whereby the annular third projectile 12 located between the middle launch tube 5 and the outer launch tube 6 is launched toward the first end surface 2 of the metal rod 1. When the third projectile 12 collides with the first end surface 2 of the metal rod 1, inside the metal rod 1, an elastic pulse waveform is generated and propagates in the metal rod 1 with a time-lag of $\alpha 2$ relative to the waveform generated by the collision of the first projectile 8.

In this way, the elastic pulse waveforms generated in the metal rod 1 give rise to a composite shock acceleration waveform in the metal rod 1, and this waveform propagates with respect to a second end surface 22 of the metal rod 1. Thus, by using a plurality of projectiles and arbitrarily setting the launch timing of each projectile, in accordance with the superposition principle, overall, it becomes possible to generate a shock acceleration waveform having a prescribed duration time.

Figure 2:
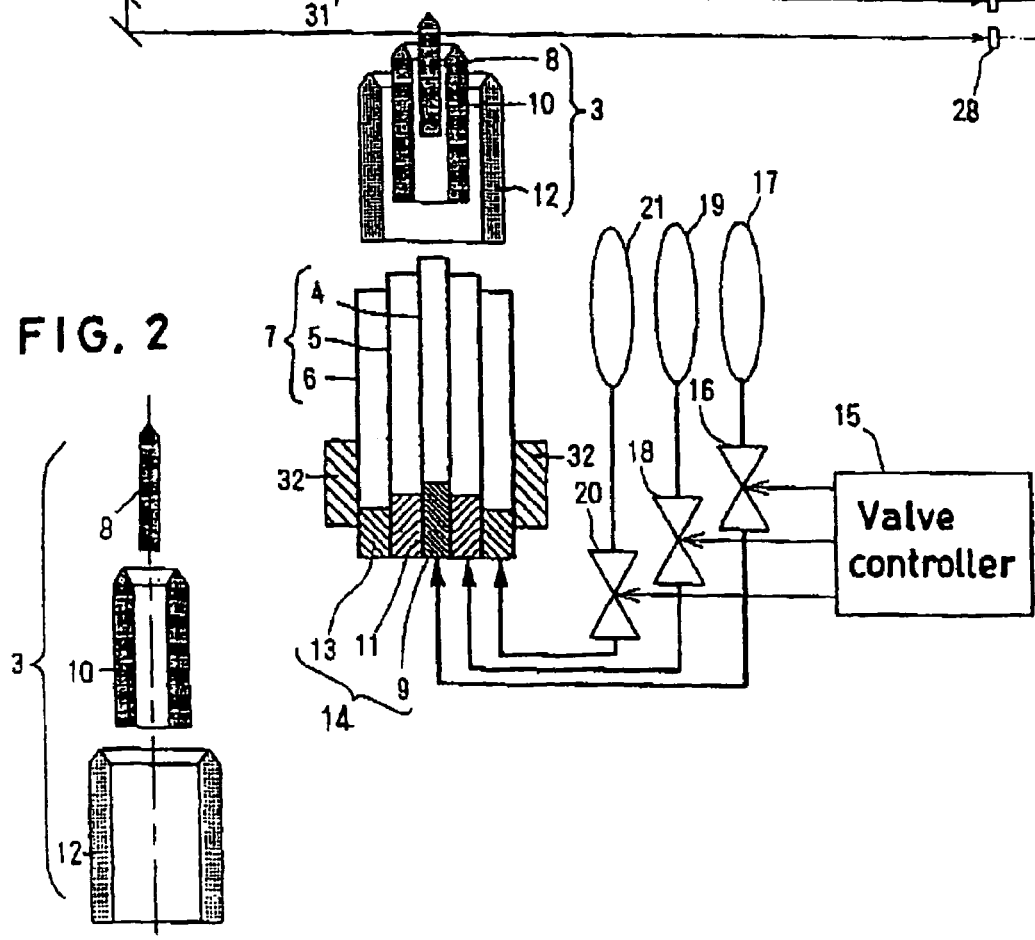
FIG. 2 is an explanatory view of an example of a set of projectiles used in the present invention.

In the illustrated embodiment, a triple launch tube is used, with FIG. 2 showing an example using three projectiles, 8, 10 and 12. However, the present invention can use from two projectiles to even greater number of n projectiles in the same way described above. It is preferable for the contact surfaces between the launch tubes 4, 5 and 6 and the projectiles 8, 10 and 12, and the peripheral surface of each projectile, to be lubrication treated or provided with a surface treatment layer that lowers the friction coefficient.

High-polymer material, plastics, wood or the like can be affixed to the tip of the projectiles to narrow the frequency band of elastic wave pulses generated in the metal rod 1 by the launch of each projectile. In this case, multilayer projectiles may be used in which the projectile body has a laminated structure of different materials, such as metal, high-polymer material, plastics, wood and so forth.

An elastic wave pulse generated at the first end surface 2 of the metal rod 1, as described above, propagates within the metal rod 1 and reaches the second end surface 22, and reflects. Shock acceleration generated normal to the end surface in the reflection process is input to a direct current acceleration sensor 23 that is the calibration object attached to that end surface. Also, the shock acceleration is measured precisely by measurement using a strain gauge 25, or a laser interferometer 24 that projects a laser beam at the second end surface 22, or by measurement using both, if necessary, and carrying out comparisons with the measured values from the acceleration sensor 23.

In the detection of the shock acceleration that is generated, when using the strain gauge 25 affixed to a side surface of the rod, the strain gauge 25 can be implemented as a single unit, or as a plurality arrayed axially along the metal rod axis, or as a plurality in the radial direction. In the embodiment shown in FIG. 1, there are three arrays of N gauges separated by $L_1$, $L_2$ and $L_N$ from the first end surface 2.

In using a plurality of strain gauges, the output signal from each gauge is input to the personal computer 26 used as a processor, and a predetermined correction function is used to obtain a result equivalent to the measured results of the laser interferometer 24. Moreover, although the above embodiment shows an example in which the laser interferometer 24 and the strain gauge 25 are used, the present invention can also be implemented using just either one.

In using the acceleration sensor calibration apparatus having the above configuration to actually carry out calibration, the theory described below can be used to carry out accurate calibration. That is, in the present invention, an internal elastic wave pulse is generated by imparting a shock by colliding a projectile against the end surface of a rod set with its center axis aligned with the direction of gravity acceleration or a rod set at an inclined angle from the vertical (hereafter described simply as rod). In the course of this, a multiplicity of projectiles n (n=1 ... N, innermost being 1, outermost being N) are launched from multiple launch tubes n (n=1 ... N, innermost being 1, outermost being N). Based on the principle of superposition, by offsetting the launch timing of projectile 2, ..., projectile N relative to projectile 1, overall, the duration time of the elastic wave pulse is increased. Lubrication treatment is applied to the contact surface between projectile n (n=1 ... N) and multiple launch tube n (n=1 ... N).

High-polymer material, plastics, wood or the like can be affixed to the tip of the projectiles to narrow the frequency band of the elastic wave pulses generated in the metal rod 1 by the launch of each projectile. Alternatively, multilayer projectiles may be used in which the projectile body has a laminated structure of different materials, such as metal, high-polymer material, plastics, wood and so forth.

The elastic wave pulse propagates in the rod until it reaches the other end surface and reflects. Shock acceleration generated normal to the end surface in the reflection process serves as an input to a direct current acceleration sensor attached to that end surface.

Detection of the generated shock acceleration is carried out using a laser interferometer or strain gauges affixed at a plurality of locations on the side surface of the rod (including the case of one location in the axial direction). When measurement is conducted using a laser interferometer, the laser is directly projected onto the rod end surface on which the direct current acceleration sensor that is the calibration object is attached.

When measurement is carried out using strain gauges, the output result from a plurality of gauges is signal processed for conversion to a strain gauge value at a representative location, thereby suppressing noise, while at the same time a correction function obtained beforehand with the laser interferometer is applied to the frequency characteristics of the gauge output at that representative location, to thereby obtain a result equivalent to the measured result obtained with the laser interferometer.

In the above, an elastic wave pulse is generated and propagates in the rod by a shock imparted by impacting a projectile on the end surface of the rod that is adequately long compared with its diameter. At the time the elastic wave pulse reaches the end surface and reflects, the end surface of the rod moves at the following acceleration that is twice the product of the propagation velocity (C) of the longitudinal elastic wave and the strain rate $\dot{\epsilon}(t)$ of the incident elastic wave pulse. [Formula 1]

$$a(t) = 2C\dot{\epsilon}(t) \quad \text{[Formula 2]}$$

In the case of multiple launch tubes n (n =1 ... N), taking $\epsilon_n$ as the strain of the incident elastic wave pulse produced by launch tubes n, the superposition principle applies to the elastic wave, so the following equation holds. Here, represents differential relating to time.

[Formula 3] (1)

$$a(t) = 2C\sum_{n=1}^{N}\dot{\epsilon}_n(t)$$

In practice, it is not possible to affix the strain gauge onto the boundary between the rod end surface and the rod side surface, so it is assumed that it is affixed at a location that is $L_n$(n=1 ... N) away from the impacted end surface of the rod. Also, $L_1$ is taken as the representative gauge location of a plurality of gauges affixed axially along the rod. In this case, at each $L_n$ (n=1 ... N) location, the wave incident on the end surface onto which the direct current acceleration sensor has been attached and the reflected wave have to be separated and observed.

Since in accordance with elastic wave propagation theory, the elastic wave pulse strain in a rod section that is far enough away from the impacted end surface will be homogenous, and so can be analytically represented at a distance z and time t (assuming the projectile impact starts at t=0) from the impacted end surface. Thus, as a plane wave, the internal strain ($\epsilon$(z,t)) of the rod can be expressed as in the following equation.

$$\epsilon(z,t) = F(z,t) \quad (2)\text{[Formula 4]}$$

F(z,t) is expressed as follows. (Skalak's solution in the case of the first term of a series solution)

[Formula 5] (3)

$$F(z,t) = \epsilon_t(t,z) - \epsilon_t\left(t - \frac{2l_p}{C_p}, z\right)$$

Here,
t: time
$l_p$: length of projectile
$C_p$: propagation velocity of longitudinal elastic wave in projectile
$\epsilon_t$(t,z): primary term of Skalak's analytic solution

[Formula 6] (4)

$$\varepsilon_t(t, z) = \frac{V_1}{\pi C}\left[\int_0^\infty \frac{\sin(\alpha_1 \eta + \eta^3/3)}{\eta} d\eta + \int_0^\infty \frac{\sin(\alpha_2 \eta + \eta^3/3)}{\eta} d\eta\right]$$

[Formula 7] (5)

$$\alpha_1 = \frac{Z - C_a t}{\left[\frac{3}{16} v^2 D_a^2 C t\right]^{\frac{1}{3}}}$$

[Formula 8] (6)

$$\alpha_2 = \frac{-Z - C_a t}{\left[\frac{3}{16} v^2 D_a^2 C t\right]^{\frac{1}{3}}}$$

Here,
$V_1$: collision velocity of projectile
t: elapsed time from collision
v: Poisson ratio
$D_a$: diameter of metal rod
z: horizontal coordinate of metal rod Next, the following procedure is used in order to make a measurement with increased sensitivity and noise resistance when a large number of strain gauges are used. The average value at the output section of a plurality of gauges at location $L_n$ (n=1 ... N) is taken as (collision starting time t=0). A wave takes time to propagate, so output signals from strain gauges at location $L_n$ (n=1 ... N) will not be in phase. So, in accordance with the following procedure, using Equation (3), the output of a gauge affixed at representative location $L_1$ can be converted to an equivalent output.

[Formula 9] (7)

$$\varepsilon_n^e(t) = L^{-1}\left[L[\varepsilon_{Ln}(t)] \frac{L\left[F\left(L_1, t - \frac{(L_n - L_1)}{C}\right)\right]}{L[F(L_n, t)]}\right]$$

$(n = 2 ... N)$

Here, [Formula 10] L and $L^{-1}$ are a Laplace operator and an inverse Laplace operator. Therefore, elastic wave pulse strain $\varepsilon_r(L_1, t)$ at the representative location can be expressed by the following equation.

[Formula 11] (8)

$$\varepsilon_r(L_1, t) = \frac{1}{N}\left[\varepsilon_{L1}(L_1, t) + \sum_{n=2}^{N} \varepsilon_n^e(t)\right]$$

In this way, by averaging the corrected output signals from a plurality of strain gauges, it is possible to reduce the effect of noise and measure minute dynamic strain, that is, it is possible to measure low peak acceleration.

When elastic wave dispersion and attenuation and the like due to the propagation of an elastic wave pulse from the representative strain gauge location to the end surface where the acceleration sensor is attached are not taken into consideration, since the distance from the representative location of the plurality of strain gauges to the end surface where the direct current acceleration sensor is attached is L-$L_1$, if $\varepsilon_r(L_1, t)$ is used, acceleration a(t) generated at the end surface where the acceleration sensor is attached can be expressed by the following equation.

[Formula 12] (9)

$$a(t) = 2C\varepsilon_r\left(L_1, t - \frac{L - L_1}{C}\right)$$

When gauge frequency response is also ignored, it is possible to obtain the frequency characteristics of the acceleration sensor shown by the following Equation (10) by comparing, in the frequency domain, the input signal to the acceleration sensor shown in the above Equation (9) with the output signal ($a_{out}(t)$) of the acceleration sensor.

[Formula 13] (10)

$$\frac{L[a_{out}(t)]}{2Cj\omega L\left[\varepsilon_r\left(L_1, t - \frac{L - L_1}{C}\right)\right]}$$

Also, based on elastic wave theory, when strain gauge output is error-corrected, with respect to the strain gauge output signal at the representative location obtained by the above Equation (9), Equation (3) is applied to obtain the strain [Formula 14] $\varepsilon_{riT}(t)$ of the elastic wave pulse incident on the end surface where the acceleration sensor is attached. For this, the following equation is used.

[Formula 15] (11)

$$\frac{L[\varepsilon_{riT}(t)]}{L[\varepsilon_r(t)]} = \frac{L[F(L, t)]}{L[F(L_1, t)]}$$

The acceleration expressing the motion of the end surface caused by the elastic pulse reflection is established from the above Equation (11), so the frequency response of the acceleration sensor is obtained in accordance with the following equation.

[Formula 16] (12)

$$\frac{L[a_{out}(t)]}{2Cj\omega L[\varepsilon_{riT}(t)]}$$

Also, when a laser interferometer is used, the velocity ($v_{iL}(t)$) of the motion of the end surface of the rod where the acceleration sensor is attached can be measured, enabling the frequency response of the acceleration sensor to be obtained from the following Equation (13).

[Formula 17] (13)

$$\frac{L[a_{out}(t)]}{L\left[\frac{dv_{iL}(t)}{dt}\right]} = \frac{L[a_{out}(t)]}{j\omega L[v_{iL}(t)]}$$

Also, when correcting gauge measurement results using a correction function relating to the strain gauge dynamic characteristics obtained using strain gauges and a laser interferometer, the fact that the following equation is established between the velocity ($v_L(t)$) of rod end surface motion measured by the laser interferometer and the strain ($\epsilon_{iL}(t)$) of the elastic wave pulse incident on the end surface is utilized.

[Formula 18] $v_L(t)=2C\epsilon_{iL}(t)$ (14)

The acceleration sensor transfer function can be obtained by multiplying the correction function ($G_{CL}(j\omega)$) of the following Equation (15) obtained by comparing the strain ($\epsilon_{iL}(t)$) of the elastic wave pulse incident on the end surface obtained by the above Equation (14) with the strain signal at the representative location in the frequency domain by the above Equation (10).

[Formula 19]

$$G_{CL}(j\omega) = \frac{L\left[\epsilon_r\left(L_1, t - \frac{L-L_1}{C}\right)\right]}{L[\epsilon_{iL}(t)]}$$ (15)

INDUSTRIAL APPLICATION

As described in the foregoing, in accordance with the present invention, an elastic wave pulse is generated in a metal rod supported in alignment with a direction of gravity acceleration or at a prescribed angle thereto by colliding a projectile against the end surface of the metal rod, an acceleration sensor is used to measure the acceleration of the motion of the other end surface of the metal rod, a laser interferometer or strain gauge is used to measure the motion of the other end surface, the measurement signal is processed and corrected, and the processed result and the measured values obtained by the acceleration sensor are used to obtain the frequency response of the direct current acceleration sensor. Therefore, the shock acceleration waveform and the frequency band can be freely controlled and the frequency characteristics of the direct current acceleration sensor that detects the direct current acceleration can be accurately and easily measured and evaluated, including evaluation of the effect of the gravity acceleration. Also, the duration time, peak value, waveform spectra and the like of the acceleration waveform imparted with respect to the direct current acceleration sensor to be calibrated can be readily controlled, enabling shock acceleration to be generated and the direct current acceleration sensor to be calibrated.

Also, low shock acceleration can be used to obtain the peak sensitivity of the direct current acceleration sensor relative to the shock acceleration, making it possible to clarify what effect the gravity acceleration value has on the peak sensitivity of the direct current acceleration sensor. It is further possible to find with high precision what effect the gravity acceleration value has on the frequency characteristics of a direct current acceleration sensor or a similar servo type acceleration sensor.

It is also possible to clarify what effect the inclination at which a direct current acceleration sensor or a similar servo type acceleration sensor is attached has on the peak sensitivity relative to the shock acceleration, and the effect that the inclination at which a direct current acceleration sensor or a similar servo type acceleration sensor is attached has on the frequency characteristics can also be obtained with high precision.

It is also possible to establish a measurement standard for a direct current acceleration sensor or a similar servo type acceleration sensor, and as it is possible to measure using strain gauges, the metal rod can be used as a transfer standard, which is particularly useful for a secondary standard.

Also, the frequency band of the generated shock acceleration can be controlled, so it is further possible to obtain resonant frequencies, making it possible to clarify the characteristics of a direct current acceleration sensor by comparing electrical resonance measurements with resonance measurements based on inputs of actual mechanical acceleration.

The invention claimed is:

1. A method for measuring frequency characteristics of a direct current acceleration sensor, comprising:
supporting a metal rod with a center axis thereof aligned with a direction of gravity acceleration,
impacting one of end surfaces of the metal rod with a projectile to generate and propagate an elastic wave pulse in the metal rod,
using a direct current acceleration sensor provided on the other of the end surfaces of the metal rod to detect an acceleration arising when the elastic wave pulse reflects at the other end surface of the metal rod,
using a strain gauge provided on a side surface of the metal rod to measure metal rod strain caused by the impact of the projectile against the other end surface of the metal rod, and
obtaining a frequency response of the direct current acceleration sensor from a signal from the direct current acceleration sensor and a signal from the strain gauge;
wherein one end surface of the metal rod is impacted with the projectile to generate the elastic wave pulse in the metal rod,
the method further comprising:
taking as an input signal to the direct current acceleration sensor provided on the other end surface of the metal rod dynamic displacement, velocity or acceleration in a direction normal to the other end surface produced when the elastic wave pulse generated by the impact of the projectile reflects at the other end surface,
using the direct current acceleration sensor to detect, and the strain gauge provided on the side surface of the metal rod to measure, the input signal having time as a function,
carrying out signal processing with respect to an output signal from the direct current acceleration sensor and an output signal from the strain gauge, and
using data that has been signal processed as a basis for measuring gain-frequency characteristics, phase-frequency characteristics and peak sensitivity of the direct current acceleration sensor in respect of each of dynamic displacement detection function, velocity detection function and acceleration detection function of the direct current acceleration sensor,
wherein the strain gauge provided on the side surface of the metal rod is composed of a plurality of strain gauges provided at different distances from the one end surface of the metal rod.

2. A method for measuring frequency characteristics of a direct current acceleration sensor, comprising:
supporting a metal rod with a center axis thereof aligned with a direction of gravity acceleration,
impacting one of end surfaces of the metal rod with a projectile to generate and propagate an elastic wave pulse in the metal rod, using a direct current acceleration sensor provided on the other of the end surfaces of the metal rod to detect an acceleration arising when the elastic wave pulse reflects at the other end surface of the metal rod, using a strain gauge provided on a side surface of the metal rod to measure metal rod strain caused by the impact of the projectile against the other end surface of the metal rod, and obtaining a frequency response of the direct current acceleration sensor from a signal from the direct current acceleration sensor and a signal from the strain gauge, wherein the one end surface of the metal rod is impacted with the projectile to generate the elastic wave pulse in the metal rod, the method further comprising:

taking as an input signal to the direct current acceleration sensor provided on the other end surface of the metal rod dynamic displacement, velocity or acceleration in a direction normal to the other end surface produced when the elastic wave pulse generated by the impact of the projectile reflects at the other end surface, using the direct current acceleration sensor to detect, and the strain gauge provided on the side surface of the metal rod to measure, the input signal having time as a function, carrying out signal processing of an output signal from the direct current acceleration sensor and an output signal from the strain gauge, carrying out error correction of the output signal from the strain gauge based on elastic wave theory, and using data that has been signal processed and error corrected as a basis for measuring gain-frequency characteristics, phase-frequency characteristics and peak sensitivity of the direct current acceleration sensor in respect of each of dynamic displacement detection function, velocity detection function and acceleration detection function of the direct current acceleration sensor, wherein the strain gauge provided on the side surface of the metal rod is composed of a plurality of strain gauges provided at different distances from the one end surface of the metal rod.

3. A method for measuring frequency characteristics of a direct current acceleration sensor, comprising:

supporting a metal rod with a center axis thereof aligned with a direction of gravity acceleration, impacting one of end surfaces of the metal rod with a projectile to generate and propagate an elastic wave pulse in the metal rod, using a direct current acceleration sensor provided on the other of the end surfaces of the metal rod to detect an acceleration arising when the elastic wave pulse reflects at the other end surface of the metal rod, using a strain gauge provided on a side surface of the metal rod to measure metal rod strain caused by the impact of the projectile against the other end surface of the metal rod, and obtaining a frequency response of the direct current acceleration sensor from a signal from the direct current acceleration sensor and a signal from the strain gauge, wherein the one end surface of the metal rod is impacted with the projectile to generate the elastic wave pulse in the metal rod, the method further comprising:

taking as an input signal to the direct current acceleration sensor provided on the other end surface of the metal rod dynamic displacement, velocity or acceleration in a direction normal the other end surface produced when the elastic wave pulse generated by the impact of the projectile reflects at the other end surface, using the direct current acceleration sensor to detect, and the strain gauge provided on the side surface of the metal rod to measure, the input signal having time as a function, carrying out signal processing of an output signal from the direct current acceleration sensor and an output signal from the strain gauge, carrying out error correction of the output signal from the strain gauge based on elastic wave theory, using a correction function relating to dynamic characteristics of the strain gauge to correct results of measurements by the gauge, and using data that has been signal processed, error corrected and measurement-result-corrected as a basis for measuring gain-frequency characteristics, phase-frequency characteristics and peak sensitivity of the direct current acceleration sensor in respect of each of dynamic displacement detection function, velocity detection function and acceleration detection function of the direct current acceleration sensor, wherein the strain gauge provided on the side surface of the metal rod is composed of a plurality of strain gauges provided at different distances from the one end surface of the metal rod.

4. A method for measuring frequency characteristics of a direct current acceleration sensor, comprising:

supporting a metal rod with a center axis thereof aligned with a direction of gravity acceleration, impacting one of end surfaces of the metal rod with a projectile to generate and propagate an elastic wave pulse in the metal rod, using a direct current acceleration sensor provided on the other of the end surfaces of the metal rod to detect an acceleration arising when the elastic wave pulse reflects at the other end surface of the metal rod, using a strain gauge provided on a side surface of the metal rod to measure metal rod strain caused by the impact of the projectile against the other end surface of the metal rod, and obtaining a frequency response of the direct current acceleration sensor from a signal from the direct current acceleration sensor and a signal from the strain gauge, wherein one end surface of the metal rod is impacted with the projectile to generate the elastic wave pulse in the metal rod, the method further comprising:

taking as an input signal to the direct current acceleration sensor provided on the other end surface of the metal rod dynamic displacement, velocity or acceleration in a direction normal to the other end surface produced when the elastic wave pulse generated by the impact of the projectile reflects at the other end surface, using the direct current acceleration sensor to detect, and the strain gauge provided on the side surface of the metal rod to measure, the input signal having time as a function, carrying out signal processing with respect to an output signal from the direct current acceleration sensor and an output signal from the strain gauge, and using data that has been signal processed as a basis for measuring gain-frequency characteristics, phase-frequency characteristics and peak sensitivity of the direct current acceleration sensor in respect of each of dynamic displacement detection function, velocity detection function and acceleration detection function of the direct current acceleration sensor, wherein the strain gauge provided on the side surface of the metal rod is composed of a plurality of strain gauges provided on the circumference at equal distances from the one end surface of the metal rod.

5. A method for measuring frequency characteristics of a direct current acceleration sensor, comprising:

supporting a metal rod with a center axis thereof aligned with a direction of gravity acceleration, impacting one of end surfaces of the metal rod with a projectile to generate and propagate an elastic wave pulse in the metal rod, using a direct current acceleration sensor provided on the other of the end surfaces of the metal rod to detect an acceleration arising when the elastic wave pulse reflects at the other end surface of the metal rod, using a strain gauge provided on a side surface of the metal rod to measure metal rod strain caused by the impact of the projectile against the other end surface of the metal rod, and obtaining a frequency response of the direct current acceleration sensor from a signal from the direct current acceleration sensor and a signal from the strain gauge, wherein the one end surface of the metal rod is impacted with the projectile to generate the elastic wave pulse in the metal rod, the method further comprising:

taking as an input signal to the direct current acceleration sensor provided on the other end surface of the metal rod dynamic displacement, velocity or acceleration in a direction normal to the other end surface produced when the elastic wave pulse generated by the impact of the projectile reflects at the other end surface, using the direct current acceleration sensor to detect, and the strain gauge provided on the side surface of the metal rod to measure, the input signal having time as a function, carrying out signal processing of an output signal from the direct current acceleration sensor and an output signal from the strain gauge, carrying out error correction of the output signal from the strain gauge based on elastic wave theory, and using data that has been signal processed and error corrected as a basis for measuring gain-frequency characteristics, phase-frequency characteristics and peak sensitivity of the direct current acceleration sensor in respect of each of dynamic displacement detection function, velocity detection function and acceleration detection function of the direct current acceleration sensor, wherein the strain gauge provided on the side surface of the metal rod is composed of a plurality of strain gauges provided on the circumference at equal distances from the one end surface of the metal rod.

6. A method for measuring frequency characteristics of a direct current acceleration sensor, comprising:

supporting a metal rod with a center axis thereof aligned with a direction of gravity acceleration, impacting one of end surfaces of the metal rod with a projectile to generate and propagate an elastic wave pulse in the metal rod, using a direct current acceleration sensor provided on the other of the end surfaces of the metal rod to detect an acceleration arising when the elastic wave pulse reflects at the other end surface of the metal rod, using a strain gauge provided on a side surface of the metal rod to measure metal rod strain caused by the impact of the projectile against the other end surface of the metal rod, and obtaining a frequency response of the direct current acceleration sensor from a signal from the direct current acceleration sensor and a signal from the strain gauge, wherein the one end surface of the metal rod is impacted with the projectile to generate the elastic wave pulse in the metal rod, the method further comprising:

taking as an input signal to the direct current acceleration sensor provided on the other end surface of the metal rod dynamic displacement, velocity or acceleration in a direction normal the other end surface produced when the elastic wave pulse generated by the impact of the projectile reflects at the other end surface, using the direct current acceleration sensor to detect, and the strain gauge provided on the side surface of the metal rod to measure, the input signal having time as a function, carrying out signal processing of an output signal from the direct current acceleration sensor and an output signal from the strain gauge, carrying out error correction of the output signal from the strain gauge based on elastic wave theory, using a correction function relating to dynamic characteristics of the strain gauge to correct results of measurements by the gauge, and using data that has been signal processed, error corrected and measurement-result-corrected as a basis for measuring gain-frequency characteristics, phase-frequency characteristics and peak sensitivity of the direct current acceleration sensor in respect of each of dynamic displacement detection function, velocity detection function and acceleration detection function of the direct current acceleration sensor, wherein the strain gauge provided on the side surface of the metal rod is composed of a plurality of strain gauges provided on the circumference at equal distances from the one end surface of the metal rod.

7. A method for measuring frequency characteristics of a direct current acceleration sensor, comprising:

supporting a metal rod with a center axis thereof aligned with a direction of gravity acceleration, impacting one of end surfaces of the metal rod with a projectile to generate and propagate an elastic wave pulse in the metal rod, using a direct current acceleration sensor provided on the other of the end surfaces of the metal rod to detect an acceleration arising when the elastic wave pulse reflects at the other end surface of the metal rod, using a strain gauge provided on a side surface of the metal rod to measure metal rod strain caused by the impact of the projectile against the other end surface of the metal rod, and obtaining a frequency response of the direct current acceleration sensor from a signal from the direct current acceleration sensor and a signal from the strain gauge, wherein one end surface of the metal rod is impacted with the projectile to generate the elastic wave pulse in the metal rod, the method further comprising:

taking as an input signal to the direct current acceleration sensor provided on the other end surface of the metal rod dynamic displacement, velocity or acceleration in a direction normal to the other end surface produced when the elastic wave pulse generated by the impact of the projectile reflects at the other end surface, using the direct current acceleration sensor to detect, and the strain gauge provided on the side surface of the metal rod to measure, the input signal having time as a function, carrying out signal processing with respect to an output signal from the direct current acceleration sensor and an output signal from the strain gauge, and using data that has been signal processed as a basis for measuring gain-frequency characteristics, phase-frequency characteristics and peak sensitivity of the direct current acceleration sensor in respect of each of dynamic displacement detection function, velocity detection function and acceleration detection function of the direct current acceleration sensor, wherein the projectile that impacts the one end surface of the metal rod is composed of a plurality of round, concentric projectiles launched from a launch apparatus that includes multiple round, concentric launch tubes, in which the launch apparatus can precisely and independently control launch timing of each projectile launched.

8. A method for measuring frequency characteristics of a direct current acceleration sensor, comprising:

supporting a metal rod with a center axis thereof aligned with a direction of gravity acceleration, impacting one of end surfaces of the metal rod with a projectile to generate and propagate an elastic wave pulse in the metal rod, using a direct current acceleration sensor provided on the other of the end surfaces of the metal rod to detect an acceleration arising when the elastic wave pulse reflects at the other end surface of the metal rod, using a strain gauge provided on a side surface of the metal rod to measure metal rod strain caused by the impact of the projectile against the other end surface of the metal rod, and obtaining a frequency response of the direct current acceleration sensor from a signal from the direct current acceleration sensor and a signal from the strain gauge, wherein the one end surface of the metal rod is impacted with the projectile to generate the elastic wave pulse in the metal rod, the method further comprising:

taking as an input signal to the direct current acceleration sensor provided on the other end surface of the metal rod dynamic displacement, velocity or acceleration in a direction normal to the other end surface produced when the elastic wave pulse generated by the impact of the projectile reflects at the other end surface, using the direct current acceleration sensor to detect, and the strain gauge provided on the side surface of the metal rod to measure, the input signal having time as a function, carrying out signal processing of an output signal from the direct current acceleration sensor and an output signal from the strain gauge, carrying out error correction of the output signal from the strain gauge based on elastic wave theory, and using data that has been signal processed and error corrected as a basis for measuring gain-frequency characteristics, phase-frequency characteristics and peak sensitivity of the direct current acceleration sensor in respect of each of dynamic displacement detection function, velocity detection function and acceleration detection function of the direct current acceleration sensor, wherein the projectile that impacts the one end surface of the metal rod is composed of a plurality of round, concentric projectiles launched from a launch apparatus that includes multiple round, concentric launch tubes, in which the launch apparatus can precisely and independently control launch timing of each projectile launched.

9. A method for measuring frequency characteristics of a direct current acceleration sensor, comprising:

supporting a metal rod with a center axis thereof aligned with a direction of gravity acceleration, impacting one of end surfaces of the metal rod with a projectile to generate and propagate an elastic wave pulse in the metal rod, using a direct current acceleration sensor provided on the other of the end surfaces of the metal rod to detect an acceleration arising when the elastic wave pulse reflects at the other end surface of the metal rod, using a strain gauge provided on a side surface of the metal rod to measure metal rod strain caused by the impact of the projectile against the other end surface of the metal rod, and obtaining a frequency response of the direct current acceleration sensor from a signal from the direct current acceleration sensor and a signal from the strain gauge, wherein the one end surface of the metal rod is impacted with the projectile to generate the elastic wave pulse in the metal rod, the method further comprising:

taking as an input signal to the direct current acceleration sensor provided on the other end surface of the metal rod dynamic displacement, velocity or acceleration in a direction normal the other end surface produced when the elastic wave pulse generated by the impact of the projectile reflects at the other end surface, using the direct current acceleration sensor to detect, and the strain gauge provided on the side surface of the metal rod to measure, the input signal having time as a function, carrying out signal processing of an output signal from the direct current acceleration sensor and an output signal from the strain gauge, carrying out error correction of the output signal from the strain gauge based on elastic wave theory, using a correction function relating to dynamic characteristics of the strain gauge to correct results of measurements by the gauge, and using data that has been signal processed, error corrected and measurement-result-corrected as a basis for measuring gain-frequency characteristics, phase-frequency characteristics and peak sensitivity of the direct current acceleration sensor in respect of each of dynamic displacement detection function, velocity detection function and acceleration detection function of the direct current acceleration sensor, wherein the projectile that impacts the one end surface of the metal rod is composed of a plurality of round, concentric projectiles launched from a launch apparatus that includes multiple round, concentric launch tubes, in which the launch apparatus can precisely and independently control launch timing of each projectile launched.

10. An apparatus for measuring frequency characteristics of a direct current acceleration sensor, comprising:

a metal rod support apparatus that supports a metal rod with a center axis thereof aligned with a direction of gravity acceleration, a launch apparatus for impacting one of end surfaces of a metal rod with a projectile to generate an elastic wave pulse in the metal rod, a direct current acceleration sensor provided on the other of the end surfaces of the metal rod to detect an acceleration arising when the elastic wave pulse reflects at the other end surface of the metal rod, a strain gauge provided on a side surface of the metal rod to measure metal rod strain caused by the impact of the projectile against the other end surface of the metal rod, a processor for calculating a frequency response of the direct current acceleration sensor from a signal from the direct current acceleration sensor and a signal from the strain gauge, including the launch apparatus for impacting the one end surface of the metal rod with the projectile to generate the elastic wave pulse in the metal rod, wherein the direct current acceleration sensor detects an input signal having time as a function that is dynamic displacement, velocity or acceleration in a direction normal to the other end surface produced when the elastic wave pulse generated by the impact of the projectile reflects at the other end surface of the metal rod, said input signal constituting an input signal to the direct current acceleration sensor provided on the other end surface, the strain gauge provided on the side surface of the metal rod measures metal rod strain caused by the impact of the projectile against the other end surface of the metal rod, and the processor carries out signal processing with respect to an output signal from the direct current acceleration sensor and an output signal from the strain gauge and uses data that has been signal processed as a basis for measuring gain-frequency characteristics, phase-frequency characteristics and peak sensitivity of the direct current acceleration sensor in respect of each of dynamic displacement detection function, velocity detection function and acceleration detection function of the direct current acceleration sensor, wherein the strain gauge provided on the side surface of the metal rod is composed of a plurality of strain gauges provided at different distances from the one end surface of the metal rod.

11. An apparatus for measuring frequency characteristics of a direct current acceleration sensor, comprising:

a metal rod support apparatus that supports a metal rod with a center axis thereof aligned with a direction of gravity acceleration, a launch apparatus for impacting one of end surfaces of a metal rod with a projectile to generate an elastic wave pulse in the metal rod, a direct current acceleration sensor provided on the other of the end surfaces of the metal rod to detect an acceleration arising when the elastic wave pulse reflects at the other end surface of the metal rod, a strain gauge provided on a side surface of the metal rod to measure metal rod strain caused by the impact of the projectile against the other end surface of the metal rod, a processor for calculating a frequency response of the direct current acceleration sensor from a signal from the direct current acceleration sensor and a signal from the strain gauge, including the launch apparatus for impacting the one end surface of the metal rod with the projectile to generate the elastic wave pulse in the metal rod, wherein the direct current acceleration sensor detects an input signal as a function of time standing for dynamic displacement, velocity or acceleration in a direction normal to the other end surface produced when the elastic wave pulse generated by the impact of the projectile reflects at the other end surface of the metal rod, said input signal constituting an input signal to the direct current acceleration sensor provided on the other end surface, the strain gauge provided on the side surface of the metal rod measures metal rod strain caused by the collision of a projectile, and the processor carries out signal processing with respect to an output signal from the direct current acceleration sensor and an output signal from the strain gauge, carries out error correction of the output signal from the strain gauge based on elastic wave theory, and uses data that has been signal processed and error corrected as a basis for measuring gain-frequency characteristics, phase-frequency characteristics and peak sensitivity of the direct current acceleration sensor in respect of each of dynamic displacement detection function, velocity detection function and acceleration detection function of the direct current acceleration sensor, wherein the strain gauge provided on the side surface of the metal rod is composed of a plurality of strain gauges provided at different distances from the one end surface of the metal rod.

12. An apparatus for measuring frequency characteristics of a direct current acceleration sensor, comprising:

a metal rod support apparatus that supports a metal rod with a center axis thereof aligned with a direction of gravity acceleration, a launch apparatus for impacting one of end surfaces of a metal rod with a projectile to generate an elastic wave pulse in the metal rod, a direct current acceleration sensor provided on the other of the end surfaces of the metal rod to detect an acceleration arising when the elastic wave pulse reflects at the other end surface of the metal rod, a strain gauge provided on a side surface of the metal rod to measure metal rod strain caused by the impact of the projectile against the other end surface of the metal rod, a processor for calculating a frequency response of the direct current acceleration sensor from a signal from the direct current acceleration sensor and a signal from the strain gauge, including the launch apparatus for impacting the one end surface of the metal rod with the projectile to generate the elastic wave pulse in the metal rod, wherein the direct current acceleration sensor detects an input signal as a function of time standing for dynamic displacement, velocity or acceleration in a direction normal to the other end surface produced when the elastic wave pulse generated by the impact of the projectile reflects at the other end surface of the metal rod, said input signal constituting an input signal to the direct current acceleration sensor provided on the other end surface, the strain gauge provided on the side surface of the metal rod measures metal rod strain caused by the collision of a projectile, and the processor carries out signal processing with respect to an output signal from the direct current acceleration sensor and an output signal from the strain gauge, carries out error correction of the output signal from the strain gauge based on elastic wave theory, uses a correction function relating to motion characteristics of the strain gauge obtained using an optical measuring instrument to correct results of measurement by the strain gauge and uses data that has been signal processed, error corrected and measurement-result corrected as a basis for measuring gain-frequency characteristics, phase-frequency characteristics and peak sensitivity of the direct current acceleration sensor in respect of each of dynamic displacement detection function, velocity detection function and acceleration detection function of the direct current acceleration sensor, wherein the strain gauge provided on the side surface of the metal rod is composed of a plurality of strain gauges provided at different distances from the one end surface of the metal rod.

13. An apparatus for measuring frequency characteristics of a direct current acceleration sensor, comprising:

a metal rod support apparatus that supports a metal rod with a center axis thereof aligned with a direction of gravity acceleration, a launch apparatus for impacting one of end surfaces of a metal rod with a projectile to generate an elastic wave pulse in the metal rod, a direct current acceleration sensor provided on the other of the end surfaces of the metal rod to detect an acceleration arising when the elastic wave pulse reflects at the other end surface of the metal rod, a strain gauge provided on a side surface of the metal rod to measure metal rod strain caused by the impact of the projectile against the other end surface of the metal rod, a processor for calculating a frequency response of the direct current acceleration sensor from a signal from the direct current acceleration sensor and a signal from the strain gauge, including the launch apparatus for impacting the one end surface of the metal rod with the projectile to generate the elastic wave pulse in the metal rod, wherein the direct current acceleration sensor detects an input signal having time as a function that is dynamic displacement, velocity or acceleration in a direction normal to the other end surface produced when the elastic wave pulse generated by the impact of the projectile reflects at the other end surface of the metal rod, said input signal constituting an input signal to the direct current acceleration sensor provided on the other end surface, the strain gauge provided on the side surface of the metal rod measures metal rod strain caused by the impact of the projectile against the other end surface of the metal rod, and the processor carries out signal processing with respect to an output signal from the direct current acceleration sensor and an output signal from the strain gauge and uses data that has been signal processed as a basis for measuring gain-frequency characteristics, phase-frequency characteristics and peak sensitivity of the direct current acceleration sensor in respect of each of dynamic displacement detection function, velocity detection function and acceleration detection function of the direct current acceleration sensor, wherein the strain gauge provided on the side surface of the metal rod is composed of a plurality of strain gauges provided at equal distances from the one end surface of the metal rod.

14. An apparatus for measuring frequency characteristics of a direct current acceleration sensor, comprising:

a metal rod support apparatus that supports a metal rod with a center axis thereof aligned with a direction of gravity acceleration, a launch apparatus for impacting one of end surfaces of a metal rod with a projectile to generate an elastic wave pulse in the metal rod, a direct current acceleration sensor provided on the other of the end surfaces of the metal rod to detect an acceleration arising when the elastic wave pulse reflects at the other end surface of the metal rod, a strain gauge provided on a side surface of the metal rod to measure metal rod strain caused by the impact of the projectile against the other end surface of the metal rod, a processor for calculating a frequency response of the direct current acceleration sensor from a signal from the direct current acceleration sensor and a signal from the strain gauge, including the launch apparatus for impacting the one end surface of the metal rod with the projectile to generate the elastic wave pulse in the metal rod, wherein the direct current acceleration sensor detects an input signal as a function of time standing for dynamic displacement, velocity or acceleration in a direction normal to the other end surface produced when the elastic wave pulse generated by the impact of the projectile reflects at the other end surface of the metal rod, said input signal constituting an input signal to the direct current acceleration sensor provided on the other end surface, the strain gauge provided on the side surface of the metal rod measures metal rod strain caused by the collision of a projectile, and the processor carries out signal processing with respect to an output signal from the direct current acceleration sensor and an output signal from the strain gauge, carries out error correction of the output signal from the strain gauge based on elastic wave theory, and uses data that has been signal processed and error corrected as a basis for measuring gain-frequency characteristics, phase-frequency characteristics and peak sensitivity of the direct current acceleration sensor in respect of each of dynamic displacement detection function, velocity detection function and acceleration detection function of the direct current acceleration sensor, wherein the strain gauge provided on the side surface of the metal rod is composed of a plurality of strain gauges provided at equal distances from the one end surface of the metal rod.

15. An apparatus for measuring frequency characteristics of a direct current acceleration sensor, comprising:

a metal rod support apparatus that supports a metal rod with a center axis thereof aligned with a direction of gravity acceleration, a launch apparatus for impacting one of end surfaces of a metal rod with a projectile to generate an elastic wave pulse in the metal rod, a direct current acceleration sensor provided on the other of the end surfaces of the metal rod to detect an acceleration arising when the elastic wave pulse reflects at the other end surface of the metal rod, a strain gauge provided on a side surface of the metal rod to measure metal rod strain caused by the impact of the projectile against the other end surface of the metal rod, a processor for calculating a frequency response of the direct current acceleration sensor from a signal from the direct current acceleration sensor and a signal from the strain gauge, including the launch apparatus for impacting the one end surface of the metal rod with the projectile to generate the elastic wave pulse in the metal rod, wherein the direct current acceleration sensor detects an input signal as a function of time standing for dynamic displacement, velocity or acceleration in a direction normal to the other end surface produced when the elastic wave pulse generated by the impact of the projectile reflects at the other end surface of the metal rod, said input signal constituting an input signal to the direct current acceleration sensor provided on the other end surface, the strain gauge provided on the side surface of the metal rod measures metal rod strain caused by the collision of a projectile, and the processor carries out signal processing with respect to an output signal from the direct current acceleration sensor and an output signal from the strain gauge, carries out error correction of the output signal from the strain gauge based on elastic wave theory, uses a correction function relating to motion characteristics of the strain gauge obtained using an optical measuring instrument to correct results of measurement by the strain gauge and uses data that has been signal processed, error corrected and measurement-result corrected as a basis for measuring gain-frequency characteristics, phase-frequency characteristics and peak sensitivity of the direct current acceleration sensor in respect of each of dynamic displacement detection function, velocity detection function and acceleration detection function of the direct current acceleration sensor, wherein the strain gauge provided on the side surface of the metal rod is composed of a plurality of strain gauges provided at equal distances from the one end surface of the metal rod.

* * * * *